(12) United States Patent
Hartlaub et al.

(10) Patent No.: US 7,776,031 B2
(45) Date of Patent: Aug. 17, 2010

(54) METHOD AND APPARATUS TO CONTROL DRUG THERAPY DOSAGES IN AN IMPLANTABLE PUMP

(75) Inventors: Jerome T. Hartlaub, New Brighton, MN (US); Duane L. Bourget, Albertville, MN (US)

(73) Assignee: Medtronic, Inc., Minneapolis, MN (US)

( * ) Notice: Subject to any disclaimer, the term of this patent is extended or adjusted under 35 U.S.C. 154(b) by 1230 days.

(21) Appl. No.: 10/921,015

(22) Filed: Aug. 18, 2004

(65) Prior Publication Data

US 2005/0020996 A1 Jan. 27, 2005

Related U.S. Application Data

(60) Division of application No. 09/804,136, filed on Mar. 12, 2001, now Pat. No. 6,796,956, which is a continuation-in-part of application No. 09/303,307, filed on Apr. 30, 1999, now abandoned.

(51) Int. Cl.
*A61K 9/22* (2006.01)
(52) U.S. Cl. .................................. 604/891.1
(58) Field of Classification Search ............. 604/890.1, 604/891.1, 500, 502, 65, 66, 67, 288.01, 604/503, 31
See application file for complete search history.

(56) References Cited

U.S. PATENT DOCUMENTS

| 4,676,248 | A | | 6/1987 | Berntson |
| 4,714,462 | A | | 12/1987 | DiDomenico |
| 4,731,051 | A | * | 3/1988 | Fischell ........................ 604/67 |
| 5,069,668 | A | | 12/1991 | Boydman |
| 5,443,486 | A | | 8/1995 | Hrdlicka et al. |
| 5,582,593 | A | * | 12/1996 | Hultman ....................... 604/65 |
| 5,832,932 | A | * | 11/1998 | Elsberry et al. ............. 128/898 |
| 6,165,155 | A | * | 12/2000 | Jacobsen et al. ............. 604/156 |
| 6,361,522 | B1 | * | 3/2002 | Scheiner et al. ............... 604/67 |
| 6,427,088 | B1 | | 7/2002 | Bowman, IV et al. |
| 6,554,822 | B1 | * | 4/2003 | Holschneider et al. ... 604/892.1 |
| 2001/0037083 | A1 | | 11/2001 | Hartlaub et al. |
| 2001/0041831 | A1 | | 11/2001 | Starkweather et al. |
| 2001/0041920 | A1 | | 11/2001 | Starkweather et al. |
| 2002/0016568 | A1 | | 2/2002 | Lebel et al. |
| 2002/0019606 | A1 | | 2/2002 | Lebel et al. |
| 2002/0049480 | A1 | | 4/2002 | Lebel et al. |
| 2002/0058906 | A1 | | 5/2002 | Lebel et al. |
| 2002/0065454 | A1 | | 5/2002 | Lebel et al. |
| 2002/0065509 | A1 | | 5/2002 | Lebel et al. |
| 2002/0065540 | A1 | | 5/2002 | Lebel et al. |

FOREIGN PATENT DOCUMENTS

| DE | 10020494 A1 | 11/2000 |
| WO | WO 01/52935 A1 | 7/2001 |
| WO | WO 01/54753 A2 | 8/2001 |

* cited by examiner

*Primary Examiner*—Nicholas D Lucchesi
*Assistant Examiner*—Christopher D Koharski
(74) *Attorney, Agent, or Firm*—Banner & Witcoff, Ltd.

(57) ABSTRACT

An implantable drug infusion pump for delivering drug therapy to a patient and which also permits a patient to deliver or self-administer an additional bolus, reduces the likelihood of over dosage or under dosage by drug dosage characteristic limitations programmed into a microprocessor memory. The dose limits define the maximum and minimum amount of drug to be delivered per unit time or otherwise, reducing the likelihood that a patient may inadvertently or deliberately interfere with a treatment regimen.

16 Claims, 5 Drawing Sheets

Decrease Drug Use:

Prevent Underdose

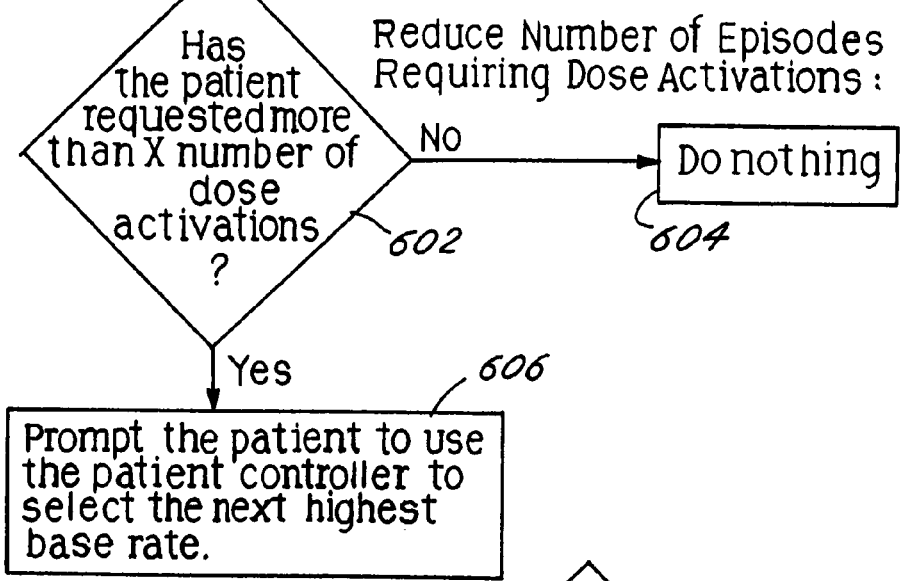
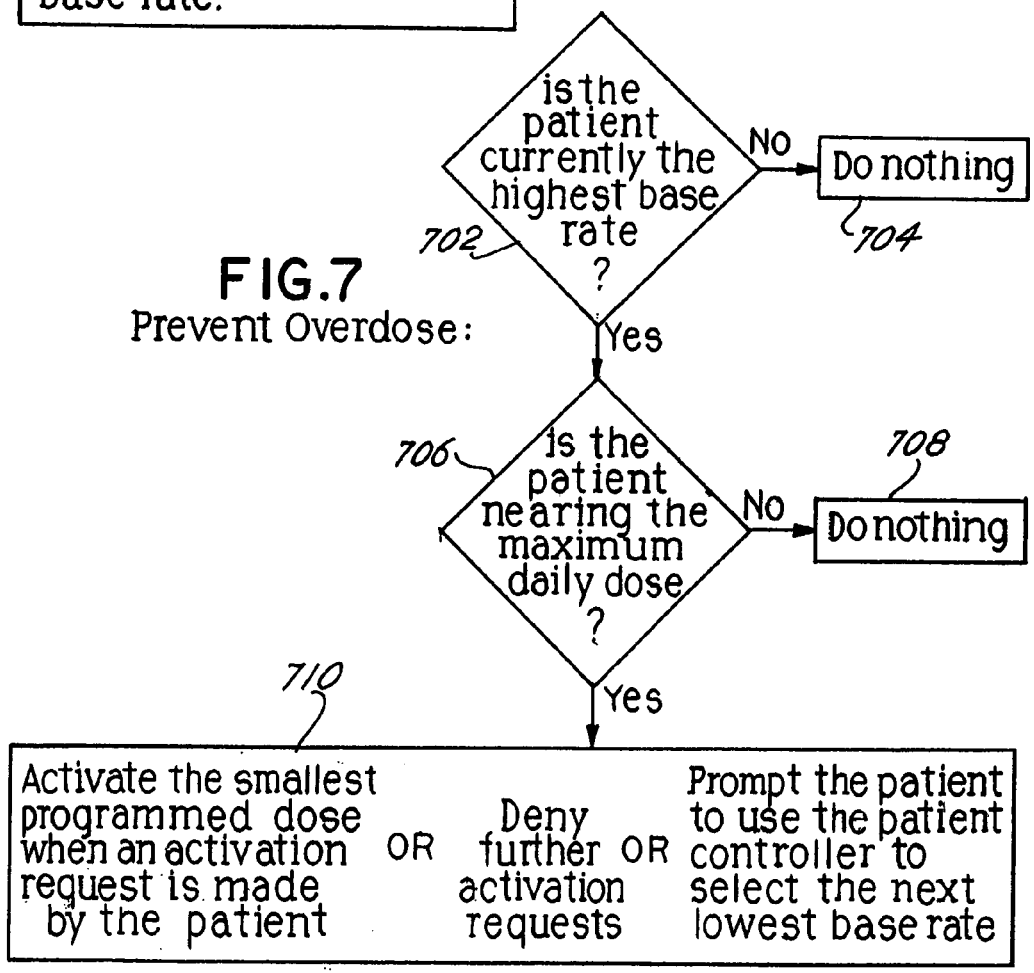

METHOD AND APPARATUS TO CONTROL DRUG THERAPY DOSAGES IN AN IMPLANTABLE PUMP

This application is a divisional of U.S. application Ser. No. 09/804,136 filed Mar. 12, 2001, now U.S. Pat. No. 6,796,956, which is a continuation-in-part of U.S. application Ser. No. 09/303,307 filed Apr. 30, 1999, now abandoned, the entire disclosures of which are hereby incorporated by reference.

FIELD OF THE INVENTION

This invention relates to implantable drug infusion pumps. In particular, this invention relates to a method and apparatus for controlling drug dosages that can be delivered by an implantable drug infusion pump.

BACKGROUND OF THE INVENTION

Implanted infusion pumps deliver therapeutic drugs to a patient according to a computer program executed by a processor that is programmed with drug dosing parameters. A microprocessor controls a small, positive displacement pump according to programming instructions delivered to the microprocessor through an RF programming link so as to permit the implantable pump to be remotely programmed and operated. In the course of executing its program, the processor controls a mechanical pump according to programmed dosage parameters.

A problem with prior art drug infusion pumps are that they run open-loop, i.e. there is no feedback mechanism controlling drug dosing. Moreover when used for treating many disorders, implantable infusion pumps need to permit the patient to self-administer a bolus of medication on demand. For example, many diabetics need to administer a bolus of insulin either just prior to or just after a meal. The changing of drug infusion rates is important as the insulin requirements of diabetic patients' change during the course of a day. Therefore, it is important that any drug treatment system be able to accommodate a predetermined constant delivery rate as well as any adjustments that may be required during the course of a day. However, this frequent changing of dosage rates can lead to potential underdosing or overdosing situations.

While prior art implantable and programmable infusion pumps permit a patient to administer additional drug dosages on demand, these prior art devices do not adequately control the amount of patient-administered dosages increasing the likelihood that a patient may overdose or underdose himself, adversely affecting the patient's physician-prescribed therapy.

A remotely programmable and implantable tissue stimulator is disclosed in U.S. Pat. No. 5,443,486 to Hrdicka et al., for a "Method and Apparatus to Limit Control of Perimeters of Electrical Tissue Stimulators." While the '486 Patent discloses a remotely programmable tissue stimulator and permits the patient to control the administration of tissue stimuli, the device disclosed in the '486 patent does not provide for programmable drug infusion therapy. Nor does the '486 provide for software-based drug infusion limits.

Programmable infusion limits in implantable infusion pumps might lessen the likelihood that a patient will overdose or underdose himself. Moreover, a software-defined limit might also lessen the likelihood that certain drug regimens will be used improperly—even by health-care providers. By using a software-defined drug dosage limit, pump manufacturers might specify certain maximum and minimum dosages for certain disorders by pre-programming their own infusion pumps with the drug dosage limitations.

In order to lessen or prevent inadvertent infused drug overdoses or underdoses, implanted drug infusion pumps require limits to be placed upon the drug delivery amount and/or frequency by health care professionals. An internal limit on the amount by which a patient can self-dose a drug, would be an improvement over the prior art implantable infusion pumps. Similar limits might prevent health care providers from inadvertently overdosing, or even underdosing treatments.

SUMMARY OF THE INVENTION

A fully implantable drug infusion pump, which includes an RF programming link, an implantable drug reservoir wherein a therapeutic drug is stored and a small, microprocessor-controlled positive displacement pump is entirely software controlled using an embedded and implantable microprocessor and power supply. Programming instructions and data delivered to the microprocessor through an RF programming link are used to limit infused drug dosage. The dosage limit data is stored in programmable memory within the microprocessor or in separate memory devices. The microprocessor controlling drug administration compares the amount of drug administered over time according to the data parameters defining the treatment regimen's dosage limits.

In the preferred embodiment of the invention, the programmable infusion pump also permits the patient to self-administer additional doses on demand. The patient-requested additional dosage limits are specified by the patient's health care provider and these limits can be programmed into the implantable pump by the health care provider using the RF programming link. Thereafter, access to the dosage limits is not available to the patient. RF programming, data encryption or other security software could limit access to the drug dosage limit data. Within the therapy program limits, patients would have the flexibility to adjust the delivery of dosages to account for meals or needed bolus flow rates during the course of the day. These changes to the base flow would be tracked by a therapy program and compared to the dosage limits. Patient notification, for example through an alarm, may be utilized if the actual dosage would fall above or below the programmed dosage limits. Patient-controlled drug dosage is limited by the health care provider-specified limit value.

In another embodiment, drug manufacturers, as well as health-care providers, might offer implantable infusion pumps for use with certain drugs that have precise treatment regimens. Over-dosing or under-dosing might be precluded by way of dosing definitions programmed into secure data storage locations.

In yet another embodiment, underdosage by the patient could be avoided if the pump is programmed to a minimum dosage or by warning the patient. The warning could be an audio alarm from the pump or an indicator on the patient's controller to which the patient could respond by increasing the dosage.

The same underdosage alarm could be implemented to alert the patient of a requested overdosage, thereby alerting the patient when a dosage request amounts to an overdosage not allowed by the pump.

BRIEF DESCRIPTION OF THE DRAWINGS

FIG. 6 illustrates a method of reducing the number of episodes requiring dose activations in accordance with an embodiment of the invention.

FIG. 7 illustrates a method of preventing a drug overdose in accordance with an embodiment of the invention.

FIG. 1 shows a simplified block diagram of the functional elements of an implantable and programmable drug infusion pump 100 having re-programmable (i.e. software-specified) dosage limits. The functional elements of the infusion pump 100 shown in FIG. 1 are small, such that the pump can be readily implanted into the abdomen of a patient for purposes of controlling chronic diseases, such as diabetes. An implanted infusion pump might also be used for acute treatment regimens, e.g. to administer chemotherapy drugs or morphine to treat cancer or treat pain respectively.

Referring to FIG. 1, a reservoir 102 contains some appropriate volume of drug to be administered to the patient by a pump 104, preferably a precision positive displacement pump drawing drug material from the reservoir 102. While FIG. 1 shows only a single reservoir and a single pump, the invention disclosed herein is readily adapted for use with multiple reservoirs for administering several different drugs or for increasing the volume of a single drug that might be implanted into the patient. Multiple pumps might be also used with multiple reservoirs to administering different drugs at different rates and times. Multiple pumps might be used with a single reservoir for increased reliability.

Figure 1:
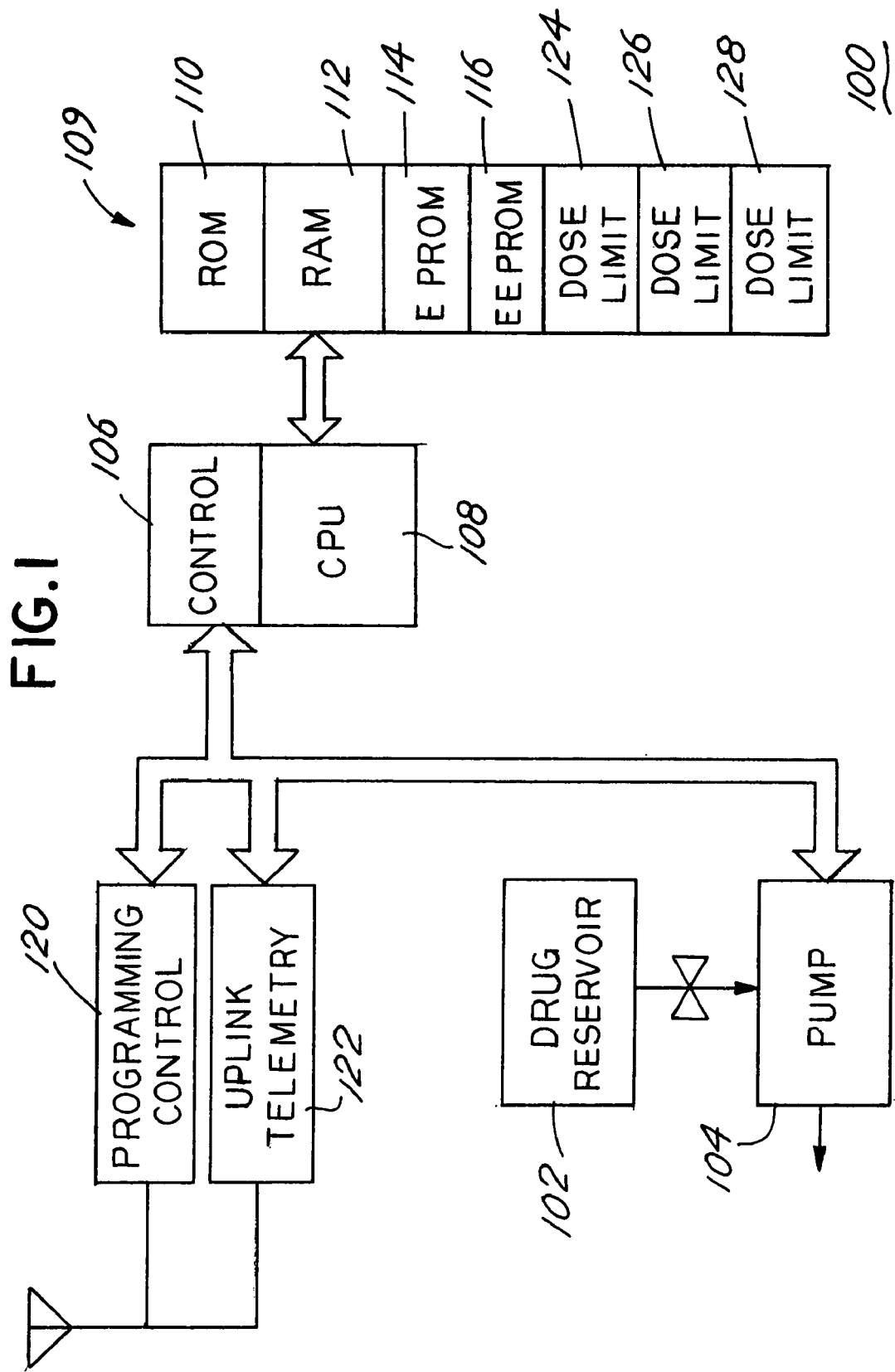
FIG. 1 discloses a simplified block diagram of an implantable, software controlled infusion pump providing software dosage limits.

The pump 104 is operatively coupled to and responsive to electrical signals delivered to it from a control unit 106. Electrical signals from the control unit 106 would, for example, start and stop the pump 104 and including its delivery rate so as to modulate the delivery of drugs from the reservoir 102 to the patient. The control circuitry within the control unit 106 would typically include appropriate electronic drive circuits, the essential function of which is to couple a central processor 108 to the pump 104 through appropriate interface circuitry well know to those skilled in the art. Alternate embodiments of the invention would of course include implementing any required pump/CPU interface directly into the microprocessor, or selecting and/or designing the pump 104 to eliminate the need for an interface between it and the low power circuits of the microprocessor. Many commercial grade microprocessors include a plethora of ancillary circuitry on a single substrate including analog-to-digital converters, digital-to-analog converters, counters, timers, clocks and so forth.

The central processor unit 108 controls the amount of drug treatment administered to the patient according to the therapy program instructions stored in a program memory 110. The program memory, which could be resident on the same semi-conductor substrate as the CPU, typically requires the ability to temporarily store and retrieve data. Random access memory 112 shown in FIG. 1 and well known to those skilled in the art, is available for use by the program executed by the CPU 108.

Those skilled in the art will recognize that while the program executed by the CPU 108 might be most economically implement in read-only-memory (ROM) structure equivalent to the ROM could include electrically programmable read only memory (EPROM) 114 as well as electrically erasable programmable read-only memory (EEPROM) 116. Both of these alternate structures are capable of retaining executable instructions required by the central processing unit 108 to operate and control the pump 100.

Figure 2:
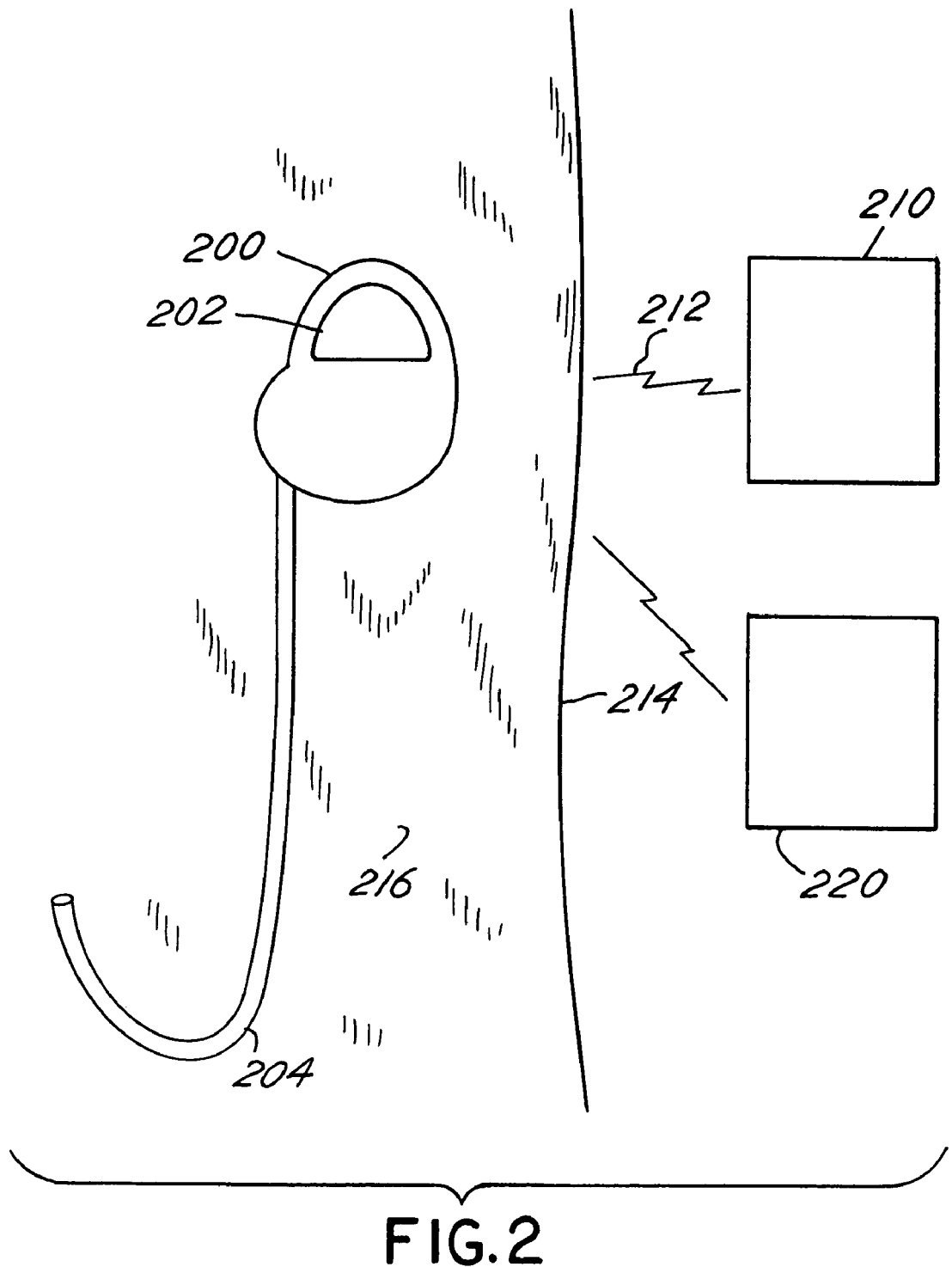
FIG. 2 shows a full system implementation of a pump including, the pump, a catheter, two external controllers, one patient use and one medical person use.

The EPROM 114 and the EEPROM 116 are re-programmable semi-conductor memories as those skilled in the art will recognize. EEPROM 116 is particularly useful in the invention as it readily lends itself as a repository for drug therapy dosage characteristics and is safer than RAM (random access memory) because RAM is volatile and susceptible to errors caused by power source interruption. EEPROM retains data for long periods of time yet is readily re-programmed by the CPU. Many commercially available microprocessors include addressable EEPROM directly on the substrate comprising the CPU further simplifying the implementation of a software-limited dosage implantable drug infusion device. FIG. 2 shows the pump system embodiment including a drug infusion pump 200 and a drug infusion catheter 204, suitable to deliver drugs to a distal sight in the body. Two external controllers are shown, one for patient use 210 and one for medical person use 220. The pump 200 with the connected catheter 204 is implanted in the patient's body 216 under the skin 214. For remote programming purposes, RF energy 212 flows bi-directionally between the pump 200 and the patient use external controller 210. Similarly, the health care provider uses an external controller 220 to independently program the implanted pump to the desire infusion parameters as is commonly done in the art. The manufacturer of the controller 220 sets the range of controller 220. A piezoelectric transducer or other suitable audio enunciator 202 on the pump body or otherwise electrically coupled to the pump and its internal controller might be used to provide an audible alarm to the patient in the case of under or overdosing.

A health care provider programs the implantable infusion pump 100 using a remote programming device 210, such as the programming device disclosed in U.S. Pat. Nos. 5,443, 486 and 4,676,248, "Circuit for Controlling a Receiver in an Implanted Device" by Berntson. The program executed by the CPU 108 regularly scans the RF link (embodied by the programming control 120 and the uplink telemetry 122) for commands. Alternate embodiments would of course include RF communication link circuits that assert an interrupt control line on so-equipped processors. At least one command recognizable by the CPU 108 is a patient-initiated request to the pump 100 to administer a bolus of drug from the reservoir 102. Such a request would be sent to the pump 100 by the patient being provided with a transponder specifically designed to transmit a bolus-request command. The functionality of the patient-operated device 210 is limited and incapable of altering key data programmed by a health care provider.

Both the health-care provided instructions and the patient requested doses are delivered to the CPU 108 through an input port on the CPU. Such an input port of the CPU 108 would include a memory mapped input/output device or other parallel or appropriate buffered serial input port, all of which are commonly found on many commercially available micro controllers.

In the course of programming, the infusion pump, the health care professional can specify a dose infusion characteristic parameter to be stored into one or more of the memory locations 124, 126 and 128 of the memory device 109 depicting FIG. 1. The dose infusion characteristic stored in memory may be one or more bytes of data (recognizable by the program instructions) to limit the amount, frequency, or other characteristic(s) of a dose of the drug to be administered to the patient by the pump 100. The dose infusion characteristics could also prescribe dosage minimum dosage amounts as well.

For example, the dose infusion characteristic stored in one of the memory locations (124, 126, 128) in FIG. 1 could be used by the program stored in ROM 110 to limit the number of drug bolus deliveries that a patient may initiate in a twenty-four hour period. Alternatively, the drug dose infusion characteristic might control the volume of drug to be delivered upon the request of the patient over a given period of time. The bolus frequency, bolus dosage size per unit time, bolus size, or other dose information might also be stored.

Similarly, a drug dose infusion characteristic might be programmed into one of the memory locations 124, 126 and 128 as fail-safe limits to prevent overdosing or underdosing a patient by a health care professional. Such an upper-limit of a drug dose might be used by the program in ROM 110 or EPROM 114, 116 as a fail safe to prevent a health care professional from accidentally overdosing or underdosing the patient. When the health care professional programs the infusion pump via the RF programming link.

In an alternate embodiment, the CPU 108 might scan or poll sensors (not shown) providing data on the efficacy of the treatment. Alternate dosages might be indicated by input from one or more sensors. Dose limits would still provide a means by which maximum or minimum treatments would not be exceeded.

Those skilled in the art will recognize that the controller 108 is preferably a programmable microcontroller or microprocessor. Such devices are well known in the electronics art and many include read-only memory, random access memory, EPROM and EEPROM on board the device. Such devices also routinely include a/d converters, d/a converters, counters, timers, and other circuits usable in a real time control application including an implantable infusion pump.

Altering embodiments might include combinational as well as sequential logic although those skilled in the art will recognize the inherent advantages of using a microprocessor or micro controller. Still other embodiments would contemplate using analog devices, such as an analog computer to control the pump 104 in response to bodily conditions.

Program instructions for the controller 108 are stored an appropriate memory device. Program instructions might also be stored in ROM, RAM, EPROM or EEPROM as set forth above. Infusion limits or dose characteristics are preferably stored in a programmable memory location, such as EPROM or EEPROM because of their ability to retain data over long periods of time, even if power is lost. In the case of random access memory (RAM) power may have to be continuously applied to the memory device and any ancillary circuitry to avoid data loss.

In operation, a health care professional would preferably download programming and/or data into the memory device 109 through the RF interlink circuitry 120 and 122. As shown in FIG. 1, these programming instructions and/or data have passed through the central processing unit 108. Depiction of this data path in FIG. 1 should not be construed as limiting. Sufficient intelligence might be built into the RF link circuitry to directly load random access memory or other memory devices 109 directly through the programming link.

Figure 3:
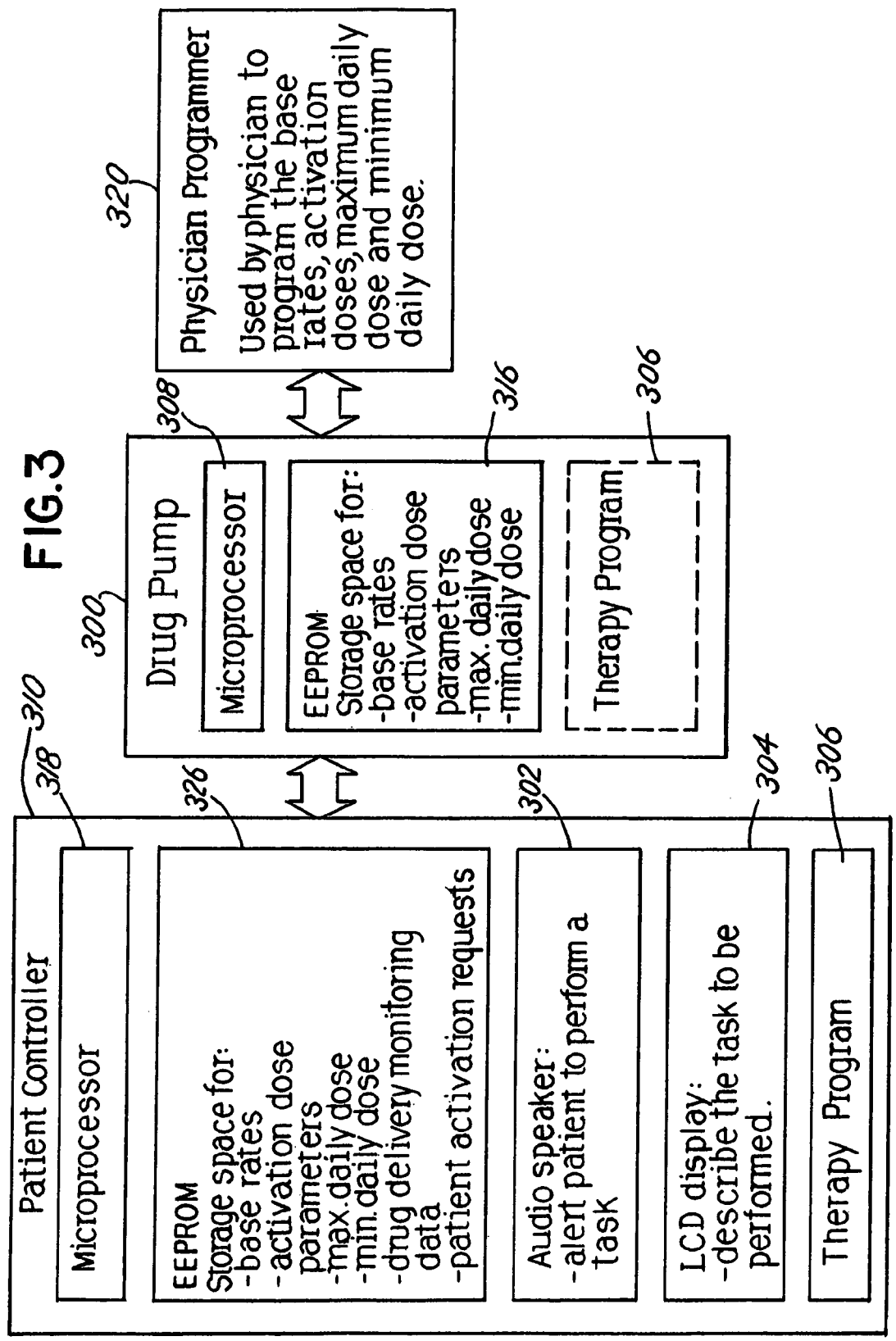
FIG. 3 shows a diagrammatic view illustrating a patient controller and a physician programmer and their communication with an implantable drug pump.

FIG. 3 represents an alternative embodiment to the configuration of the patient controller 310 and the physician programmer 320. In this embodiment, the patient controller 310 contains a therapy program 306 for possible drug infusion rate adjustments. The patient controller 310 also contains a microprocessor 318 and memory 326 that would store treatment information such as base rate drug flows, the maximum and minimum daily allowable doses, patient activation requests, and drug delivery monitoring data. The health care provider would use the physician programmer 320 to specify the drug infusion characteristics that may include the maximum and minimum daily allowance dosages, 24 hour rolling average rate limits, nominal dosage rates, and a minimum time interval between bolus requests. In particular, the health care provider may program two or more different base infusion rates that would be acceptable in reaching the daily dosages. The nominal dosage rates would be the default rates and a patient could then select a different base rate using the patient controller 310 depending on the needed amount of therapy at any given time of the day. The patient controller 310 through the therapy program 306 would only allow a base rate change to those rates already approved by the health care professional.

Optionally, the patient controller 310 may also contain a notification mechanism to provide feedback to the patient. For example and without limitation, the patient controller 310 may contain an audio speaker 302 and a LCD display 304 to provide the patient with alarm, status and task information. The alarm information would be generated from the changes in the patient controller therapy program output. A brief overview of some of the steps that the therapy program would perform in determining whether the proper amount of drugs are being administered are shown in FIGS. 4, 5, 6, and 7. These steps generally track drug infusion characteristics and allows the patient to adjust the therapy to provide a more efficient and effective drug treatment.

Figure 4:
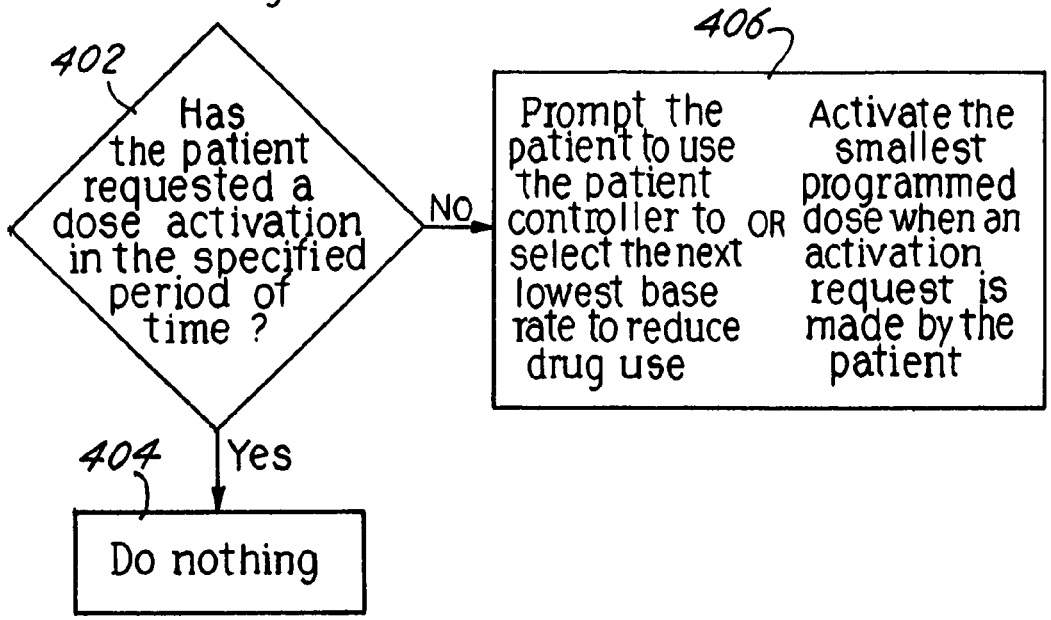
FIG. 4 illustrates a method of decreasing drug use in accordance with an embodiment of the invention.

FIG. 4 illustrates the steps that may be performed by the therapy program to determine whether the amount of drug being administered should be decreased. This may occur, for example, when the patient is not administering any additional bolus of drug, thereby suggesting that the base rate could possibly be reduced. In step 402, the therapy program determines whether the patient has requested a dose of medication in a specified period of time. This dose request by the patient could be either a bolus dose or an increase in the base rate. The specified period of time would depend on the type of drug being administered and may be, for example, based one or more days or one or more hours. If the patient has requested dose activation within the specified period of time, then the program does not make any changes, at step 404. If, on the other hand, the patient has not requested a dose indication within the specified time, at step 406, then the drug therapy could be reduced. Either the patient would be prompted, by the notification mechanism, to use the patient controller to select the next lowest base rate to reduce drug usage, or the therapy program could activate the smallest programmed dose when the patient makes an activation request. These steps ensure that a patient is not being over medicated by a base infusion rate flow that is larger than the patient's current medication requirements.

Figure 5:
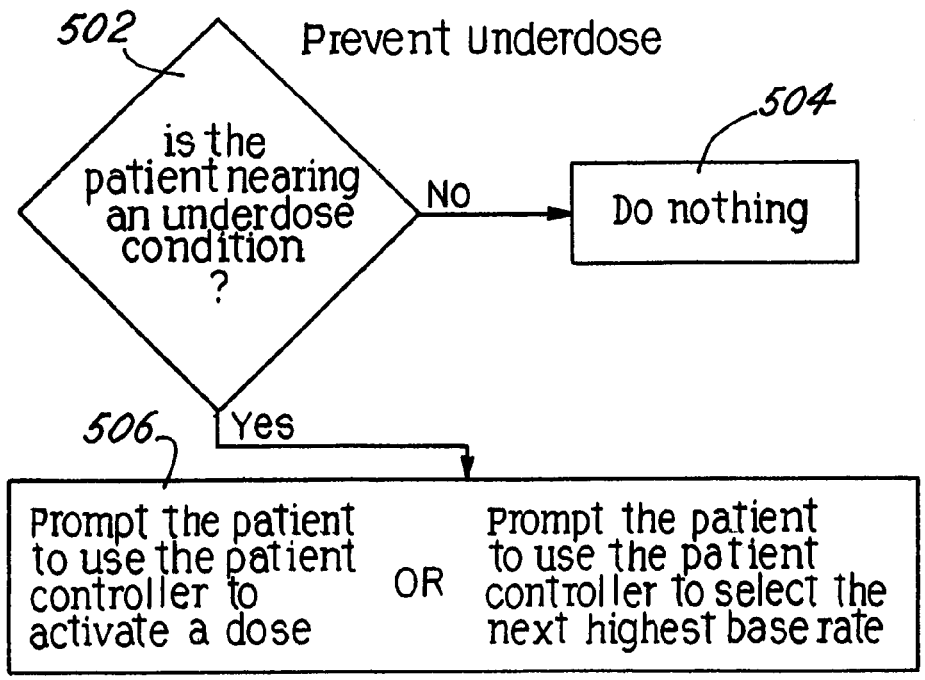
FIG. 5 illustrates a method of preventing drug underdosage in accordance with an embodiment of the invention.

FIG. 5 illustrates the steps that may be performed by the therapy program to prevent drug underdosage. In step 502, the therapy program determines whether a patient is nearing an underdosage condition. The program tracks the patient drug therapy and therefore, knows the actual total dosage being delivered to the patient. The actual total dosage delivered to the patient is the combination of the base rate and the number of bolus activations over the specified time period. The program also knows the minimum allowed dosage that is desired for a particular drug. The program compares the actual dosage and the minimum allowed dosage. If the actual dosage is within a predetermined percentage of the minimum allowed dosage then the patient is nearing an underdosage condition. This tracking of the total dosage allows flexibility in the administering of the drug therapy. For example, the physician may prescribe a base rate over the course of a period of time below the minimum dosage with the knowledge that the patient will be administering a number of bolus dosages during that period of time. The combination of the base rate and the bolus dosage activations over the course of that time period would together reach the minimum allowed dosage. If the patient is not nearing an underdosage condition then the therapy program does not make any changes at step 504. If, however, the therapy program determines that a patient is nearing an underdosage condition then the therapy program may prompt the patient, through the client notification system, to use the patient controller to either activate a bolus dose of medication or to use the next highest base rate as depicted in step 506. This reminds the patient to make sure that they administer their bolus dosages. This type of notification is important, as preventing underdosing is important in many drug therapy plans. For example, in the case of Baclofen for spasticity, drug withdrawal has serious side effects and is a major concern.

FIG. 6 illustrates the steps that may be performed by the therapy program to determine whether the patient has requested too many bolus activations over a specified period of time. In step 602, the therapy program determines whether the patient has requested more bolus activations than allowed by the health care provider. Because the program tracks the patient drug therapy, the program knows the number of bolus activations and bolus activation requests over a specified time period. If the number of bolus activations is below the allowable amount, then the therapy program continues in its normal fashion at step 604. If, however, the patient has had more than the allowed number of drug bolus activations then the patient would be prompted by the notification mechanism to use the patient controller to select a higher base rate in an attempt to reduce the amount of future bolus activation requests.

FIG. 7 illustrates the steps that may be performed by the therapy program to prevent a drug overdosage. In step 702, it is determined whether the patient is currently utilizing the highest base rate allowed by the health care provider. Because the program tracks the patient drug therapy, the program knows the current base rate and the highest base rate programmed by the physician. If the patient is not at the highest base rate then the therapy program continues as normal at step 704. However, if the base rate is at the highest allowable setting then the therapy program determines whether the patient is nearing his or her maximum daily dose at step 706. If the patient is not nearing his or her maximum daily dose then the therapy program stops the inquiry and continues as normal at step 708. However, if the patient is nearing the maximum daily dose then the therapy program could deny further activation requests, activate the smallest programmed dose when an activation request is made by the patient or prompt the patient to select the next lowest base rate.

By use of the invention disclosed herein, the likelihood of overdosing a patient with a drug from an implanted and therefore an inaccessible diffusion pump is reduced. Software based limits programmed into a microcomputer increased the flexibility of the implanted pump for a wider range of therapies compared to prior art, hard-wired devices. The software-based limits add an increased level of safety not found in prior art implantable drug infusion pumps devices.

The description of the apparatus of this invention is not intended to be limiting but is merely illustrative of the preferred embodiment of this invention. Those of ordinary skill in the art will recognize that modifications can be made without departure from the true spirit and scope of the invention.

The true spirit and scope of the inventions of this specification are best defined by the appended claims, to be interpreted in light of the foregoing specification. Other apparatus which incorporate modifications or changes to that which has been described herein are equally included within the scope of the following claims and equivalents thereof. Therefore, to particularly point out and distinctly claim the subject matter regarded as the invention, the following claims conclude this specification.

What is claimed is:

1. A method for providing a drug therapy in an automatic drug therapy delivery system, the method comprising:
   (a) implanting at least one implantable pump into a patient;
   (b) programming a dose infusion characteristic value into a programmable memory location using a radio frequency signal, the dose infusion characteristic value selected from the group consisting of a base rate drug flow, a maximum allowable dose for a predetermined period of time, a minimum allowable dose for a predetermined period of time, a patient activation request, drug monitoring delivery data, a rolling average rate limit for a predetermined period of time, a nominal dosage rate, and a minimum time interval between bolus requests;
   (c) delivering using the at least one implantable pump, in response to a patient originated stimulus, a bolus of a first drug to the patient in response to an input signal received by a programmable controller upon the determination of the programmable controller that the bolus is compliant with the dose infusion characteristic;
   (d) determining a first amount of the first drug and a second amount of a second drug delivered to the patient;
   (e) determining whether there exists a risk of overdosage or underdosage of the drug therapy;
   (f) if a risk of overdosage or underdosage is determined, notifying the patient;
   (g) sensing an efficacy of a treatment based on the first drug and the second drug; and
   (h) determining a first alternative dosage of the first drug and a second alternative dosage of the second drug from the sensed efficacy.

2. The method of claim 1 wherein the dose infusion characteristic limits the drug bolus frequency.

3. The method of claim 1 wherein the dose infusion characteristic limits the drug bolus size.

4. The method of claim 1 wherein the dose infusion characteristic limits the drug bolus frequency and size.

5. The method of claim 1 wherein the dose infusion characteristic is programmed into the programmable controller by a patient care provider.

6. The method of claim 1 wherein the programmable controller is programmable using a radio frequency programming link.

7. The method of claim 1, further comprising:
   sensing efficacy of the bolus.

8. The method of claim 1, wherein the alternative dosage is limited by a dose limit.

9. A method of providing controlled treatment therapy to a patient using at least one implantable pump, comprising:
   (a) implanting at least one implantable pump into a patient;
   (b) receiving from a health care provider a set of drug dosage limit information for a first drug and a second drug describing at least one drug therapy dosage limit, the at least one drug therapy limit selected from the group consisting of a base rate drug flow, a maximum allowable dose for a predetermined period of time, a minimum allowable dose for a predetermined period of time, a patient activation request, drug monitoring delivery data, a rolling average rate limit for a predetermined period of time, a nominal dosage rate, and a minimum time interval between bolus requests;

(c) receiving from the patient drug delivery instructions describing a first amount for a first drug and a second amount for a second drug to be delivered;

(d) storing in memory historical information relating to the first and second amounts delivered to the patient;

(e) sensing an efficacy of the first and second drugs delivered to the patient based on the historical information; and (f) separately administering the first drug and the second drug based on the sensed efficacy using the at least one implantable pump.

10. The method of claim 9, further comprising:
displaying feedback in the form of a notification mechanism if the drug delivery approaches the drug therapy dosage limit.

11. The method of providing a controlled treatment therapy of claim 10, wherein the notification mechanism is a LCD display.

12. The method of providing a controlled treatment therapy of claim 10, wherein the notification mechanism is an enunciator.

13. The method of providing a controlled treatment therapy of claim 9, wherein the drug dosage limit information is selected from the group consisting of maximum daily dosage, minimum daily dosage, and bolus dosage.

14. The method of claim 9, further comprising:
determining an alternate dosage based on the sensed efficacy, the alternate dosage limited by a dose limit.

15. An apparatus that is implantable into a patient and that provides a drug therapy, the apparatus comprising:
a processor;
a memory having stored therein machine executable instructions, that when executed, cause the apparatus to:
sense an efficacy of a treatment, wherein the treatment incorporates a first drug and a second drug; and
separately administer within the patient the first drug and the second drug based on the sensed efficacy and a dose infusion characteristic value selected from the group consisting of a base rate drug flow, a maximum allowable dose for a predetermined period of time, a minimum allowable dose for a predetermined period of time, a patient activation request, drug monitoring delivery data, a rolling average rate limit for a predetermined period of time, a nominal dosage rate, and a minimum time interval between bolus requests using at least one implantable pump.

16. The apparatus of claim 15, wherein the instructions further cause the apparatus to:
administer the first drug and the second drug at different rates and different times.

* * * * *